(12) United States Patent
Klassen et al.

(10) Patent No.: US 11,446,017 B2
(45) Date of Patent: Sep. 20, 2022

(54) EYELID EVERSION TOOL

(71) Applicant: NatureZone Inc., Toronto (CA)

(72) Inventors: Helen Mary Ann Klassen, Toronto (CA); Zachary Ralph Vanderwel, Hamilton (CA)

(73) Assignee: NatureZone Inc., Toronto (CA)

( * ) Notice: Subject to any disclaimer, the term of this patent is extended or adjusted under 35 U.S.C. 154(b) by 269 days.

(21) Appl. No.: 16/854,974

(22) Filed: Apr. 22, 2020

(65) Prior Publication Data
US 2021/0330313 A1    Oct. 28, 2021

(51) Int. Cl.
*A61B 17/02* (2006.01)
*A61B 17/00* (2006.01)
*A61B 3/14* (2006.01)

(52) U.S. Cl.
CPC ............ *A61B 17/0231* (2013.01); *A61B 3/14* (2013.01); *A61B 2017/0023* (2013.01); *A61B 2017/00424* (2013.01); *A61B 2017/00862* (2013.01)

(58) Field of Classification Search
CPC .................. A61B 17/0231; A61B 3/14; A61B 2017/0023; A61B 2017/00424; A61B 2017/00862
USPC ................... 600/210, 236; D24/133; D28/36
See application file for complete search history.

(56) References Cited

U.S. PATENT DOCUMENTS

| | | | | |
|---|---|---|---|---|
| 2,392,694 A | * | 1/1946 | Rector | A45D 2/48 |
| | | | | 132/217 |
| D210,180 S | * | 2/1968 | Solomon | A41G 5/02 |
| | | | | D28/36 |
| 3,547,135 A | * | 12/1970 | Roos | A41G 5/02 |
| | | | | D28/36 |
| 3,625,229 A | | 12/1971 | Silson | |
| 3,670,742 A | * | 6/1972 | Weaner | A41G 5/02 |
| | | | | 132/216 |

(Continued)

FOREIGN PATENT DOCUMENTS

| CN | 2166772 Y | 6/1994 |
|---|---|---|
| CN | 201253291 Y | 6/2009 |

(Continued)

OTHER PUBLICATIONS

International Search Report & Written Opinion dated Jul. 7, 2021; WIPO: Application No. PCT/CA2021/050473.

*Primary Examiner* — Eduardo C Robert
*Assistant Examiner* — David C Comstock
(74) *Attorney, Agent, or Firm* — Rowand LLP

(57) ABSTRACT

An eyelid eversion tool and a pair of disposable grippers for use with an eyelid eversion tool is described. The eyelid eversion tool includes a first arm and a second arm extending from a common joint end, the arms each, respectively, having a distal end opposite the common joint end; a first gripper fitted to the distal end of the first arm, the first gripper having a contact surface on an inward facing side thereof; and a second gripper fitted to the distal end of the second arm, the second gripper having a contact surface on an inward facing side thereof, where the contact surfaces face each other and are spaced apart, and the contact surfaces come into contact when the arms are compressed together, and where at least one of the grippers has an extender tab protruding from an outward facing side opposite its contact surface.

19 Claims, 6 Drawing Sheets

(56) References Cited

U.S. PATENT DOCUMENTS

| | | | |
|---|---|---|---|
| 4,257,406 A * | 3/1981 | Schenk | A61F 9/007 |
| | | | 606/198 |
| 4,791,944 A | 12/1988 | Stein | |
| 5,007,913 A | 4/1991 | Dulebohn et al. | |
| D355,455 S | 2/1995 | Stolte | |
| 6,299,617 B1 | 10/2001 | Stamler | |
| 6,440,065 B1 * | 8/2002 | Hered | A61B 17/0231 |
| | | | 600/236 |
| D515,242 S * | 2/2006 | Cho | A61F 9/007 |
| | | | D28/55 |
| D748,784 S | 2/2016 | Weitkamp | |
| 9,433,421 B2 | 9/2016 | Ueno et al. | |
| 2002/0103421 A1* | 8/2002 | Putrino | A61B 17/0231 |
| | | | 600/209 |
| 2005/0222612 A1 | 10/2005 | Vries et al. | |
| 2009/0217939 A1* | 9/2009 | Rabe | A41G 5/02 |
| | | | 132/218 |
| 2018/0116497 A1* | 5/2018 | Patterson | A61F 9/00 |
| 2020/0196694 A1* | 6/2020 | Lotti | B25B 9/02 |

FOREIGN PATENT DOCUMENTS

| | | |
|---|---|---|
| CN | 203524638 U | 4/2014 |
| CN | 211633225 U | 10/2020 |

\* cited by examiner

700

710

EYELID EVERSION TOOL

FIELD

The present application generally relates to medical instruments, and more particularly, to an eyelid eversion tool.

BACKGROUND

It is estimated that 18% of Americans have been diagnosed with Dry Eye Disease, and as high as 30% of the population may have the disease but are as yet undiagnosed. Typically, Dry Eye Disease was found to be more prevalent in the aging population, particularly post-menopausal women, however it is now impacting younger people across both sexes and is attributed mostly to the rise in smartphone and computer use.

Dry eye is a multifactorial disease of the ocular surface characterized by a loss of homeostasis of the tear film and accompanied by ocular symptoms in which tear film instability and hyperosmolarity (ocular surface inflammation and damage) and neurosensory abnormalities play etiological roles. It has been concluded that the leading cause of Dry Eye Disease is Meibomian Gland Dysfunction (MGD). MGD is a broad term that defines any functional abnormality of the meibomian glands.

The meibomian glands are located in and run perpendicular to the upper and lower eyelids. There are 30-40 meibomian glands in the upper lid and 20-30 in the lower lid. They differ in number, in secretory volume, and length. The meibomian glands provide the lipids that comprise the majority of the superficial layer of the tear film, and serve to prevent the evaporation of the aqueous layer. The glands are important contributors to the health of the ocular surface. When functional disruption of the meibomian glands occurs, the quality and quantity of meibum (an oily substance that prevents evaporation of the eye's tear film) changes, resulting in a negative impact on the ocular surface.

Diagnosis of MGD requires both meibography and assessment of the expressibility and quality of the meibum in both the upper and lower meibomian glands. Meibography allows observation of meibomian glands in an objective and repeatable manner. It is used to assess gland health including gland drop-out, atrophy, truncation and other abnormalities associated with MGD. Currently available meibographers not only provide clear images of the patient's meibomian glands but also support the storage of patient images that allow for comparison and tracking over time.

Comparison and tracking over time are important to both disease management and patient engagement. Recent developments suggest that gland atrophy, historically believed to be permanent, may be reversible with appropriate treatment. MGD is a chronic condition that requires treatments by an eye care professional supported by at-home care by the patient. As in any chronic disease state, patient engagement and compliance is key to success. Patient understanding of the disease and the ability to see, over time, that they can make an impact to disease management is important. Showing a patient a meibography image of their own meibomian glands and showing change over time is beneficial to encouraging their ongoing participation in their own care.

Imaging and clinical evaluation of both the upper and lower lids is required in order to best examine meibomian gland structure and function. To visualize the meibomian glands the lids must be everted. The lower lid can be everted easily with a Q-tip in one hand and simple motion. The upper lid proves to be more challenging, requiring the use of both hands. This is typically done with a finger of one hand and Q-tip in the other. A significant challenge is that one has to reach around the meibographer with both hands to evert the upper lid, bring the patient forward to rest on the forehead and chin rest, then bring the lid into focus and capture the image. Often, what occurs in practice is that only the lower lid meibomian glands are assessed and imaged.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DETAILED DESCRIPTION

Figure 1:
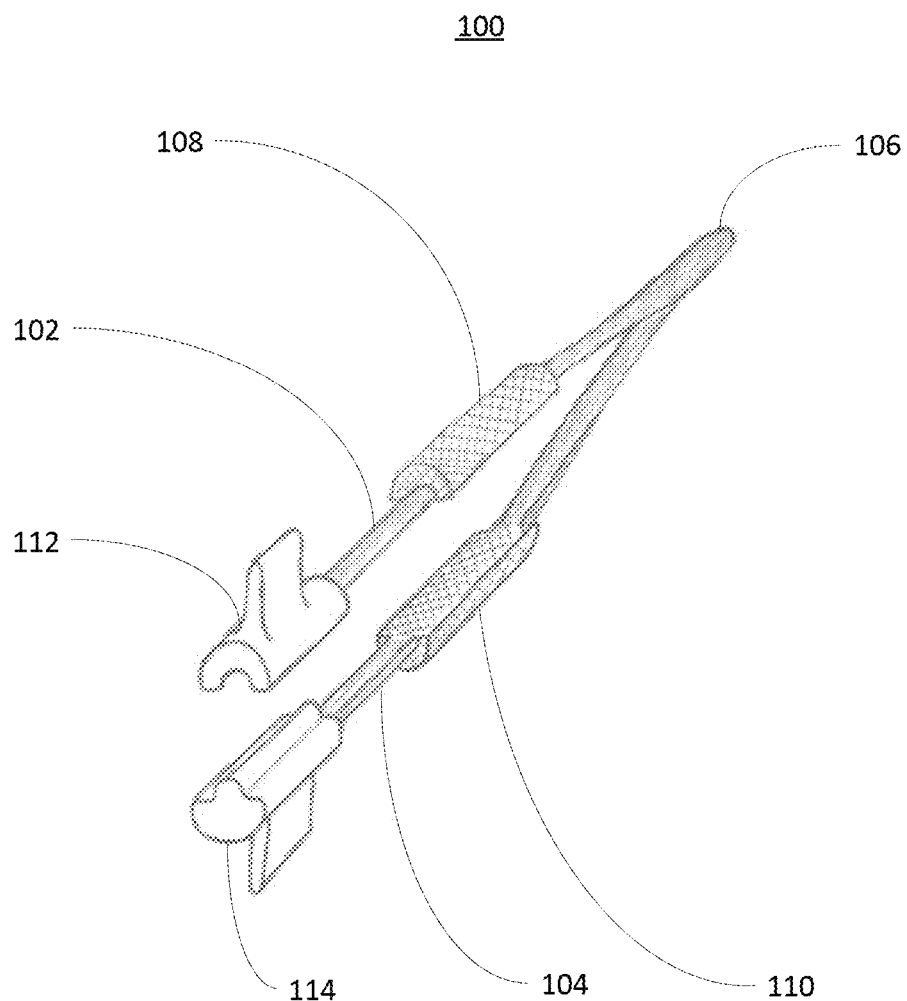
FIG. 1 is a perspective view of an example eyelid eversion tool.

In a first aspect, the present application describes an eyelid eversion tool. The tool may include a first arm and a second arm extending from a common joint end, the first arm and the second arm each, respectively, having a distal end opposite the common joint end; a first gripper fitted to the distal end of the first arm, the first gripper having a contact surface on an inward facing side thereof; and a second gripper fitted to the distal end of the second arm, the second gripper having a contact surface on an inward facing side thereof, wherein the contact surfaces face each other and are spaced apart, and the contact surfaces come into contact when the first arm and the second arm are compressed with respect to one another, and wherein at least one of the first gripper and the second gripper has an extender tab protruding from an outward facing side opposite its contact surface.

In some implementations, the common joint end is fused and provides elastic deformation when the arms are compressed with respect to one another.

In some implementations, the tool further includes a first handgrip on the first arm and a second handgrip on the second arm, the first handgrip and the second handgrip each, respectively, disposed between a distal end and the common joint end. In some cases, the first arm, the second arm, the first handgrip, and the second handgrip are all integrally formed as one unit. In some examples, the first handgrip and the second handgrip are partially rounded to provide ease of rotation to a user of the tool. In some such examples, the first handgrip and the second handgrip are semi-cylindrical in shape and each handgrip extends axially along a length of its respective arm, and the first handgrip and the second handgrip may together form a cylindrical shape when the arms are compressed with respect to one another and the contact surfaces come into contact.

In some implementations, the common joint end is hinged and resiliently biased in an open position to provide mechanical resistance when the arms are compressed with respect to one another.

In some implementations, the first gripper is friction fit onto the distal end of the first arm and the second gripper is friction fit onto the distal end of the second arm.

In some implementations, each of the first gripper and the second gripper has a keyed axial bore, and wherein each of the first arm and the second arm has a corresponding keyed profile matching the keyed axial bore.

In some implementations, the first gripper and the second gripper are made of silicone.

In some implementations, the first gripper and the second gripper are disposable.

In some implementations, the contact surface of the first gripper defines a groove extending longitudinally parallel to an axis in which the first arm extends and the contact surface of the second gripper defines a raised tongue extending longitudinally parallel to an axis in which the second arm extends, and wherein the tongue fits into the groove when the contact surfaces come into contact.

In some implementations, the protruding extender tab extends longitudinally along at least a portion of the length of the at least one of the first gripper and the second gripper, and wherein the protruding extender tab is shaped to narrow at an arcuate tip from a wider base at the outward facing side of the at least one of the first gripper and the second gripper.

In some implementations, each of the first gripper and the second gripper has the extender tab protruding from its respective outward facing side opposite its contact surface.

In a second aspect, the present application describes a pair of disposable grippers for use with an eyelid eversion tool. The pair of disposable grippers may include a first disposable gripper having a contact surface on a first side thereof; and a second disposable gripper having a contact surface on a first side thereof, wherein at least one of the first disposable gripper and the second disposable gripper has an extender tab protruding from a second side opposite its contact surface.

In some implementations, each of the first disposable gripper and the second disposable gripper has a keyed axial bore shaped to match a corresponding keyed profile of an eyelid eversion tool arm.

In some implementations, the first disposable gripper and the second disposable gripper are made of silicone.

In some implementations, the contact surface of the first disposable gripper defines a groove extending longitudinally along a length of the first disposable gripper and the contact surface of the second disposable gripper defines a raised tongue extending longitudinally along a length of the second disposable gripper, and wherein the tongue fits into the groove when the contact surfaces come into contact.

In some implementations, the protruding extender tab extends longitudinally along at least a portion of the length of the at least one of the first disposable gripper and the second disposable gripper, and wherein the extender tab is shaped to narrow at an arcuate tip from a wider base at the second side of the at least one of the first disposable gripper and the second disposable gripper.

In some implementations, each of the first disposable gripper and the second disposable gripper has the extender tab protruding from its respective second side opposite its contact surface.

Other aspects and features of the present application will be understood by those of ordinary skill in the art from a review of the following description of examples in conjunction with the accompanying figures.

In the present application, the terms "about", "approximately", and "substantially" are meant to cover variations that may exist in the upper and lower limits of the ranges of values, such as variations in properties, parameters, and dimensions. In a non-limiting example, the terms "about", "approximately", and "substantially" may mean plus or minus 10 percent or less.

In the present application, the term "and/or" is intended to cover all possible combinations and sub-combinations of the listed elements, including any one of the listed elements alone, any sub-combination, or all of the elements, and without necessarily excluding additional elements.

In the present application, the phrase "at least one of . . . or . . . " is intended to cover any one or more of the listed elements, including any one of the listed elements alone, any sub-combination, or all of the elements, without necessarily excluding any additional elements, and without necessarily requiring all of the elements.

Reference is first made to FIG. 1, which is a perspective view of an example eyelid eversion tool 100. The tool 100 includes a first arm 102 and a second arm 104, a first handgrip 108 and a second handgrip 110, and a first gripper 112 and a second gripper 114. As illustrated, the first arm 102 and the second arm 104 both extend from a common joint end 106, and each, respectively, has a distal end opposite the common joint end 106. In one embodiment, the common joint end 106 is fused and thus provides elastic deformation when the arms are compressed with respect to one another (in a tweezer-like motion). The arms may, for example, be fused at the common joint end 106 using adhesive or a fastener. In some implementations the complete tool 100, with the exception of the grippers 112, 114, is integrally formed as one single unit, i.e. the connected first arm 102, second arm 104, first handgrip 108, and second handgrip 110 may be formed in a pre-machined mold by injection molding, multi-material injection molding, or other such processes. The components of the tool 100 may, for example, be made of metal, plastic, rubber, other polymers, or any combination of materials. In another embodiment, the common joint end 106 is hinged and resiliently biased in an open position to provide mechanical resistance when the arms are compressed with respect to one another.

The eyelid eversion tool 100 includes a first handgrip 108 on the first arm 102 and a second handgrip 110 on the second arm 104. Each handgrip 108, 110 is disposed between a distal end of its respective arm and the common joint end 106. In one embodiment, the first handgrip 108 and the second handgrip 110 may be partially rounded, that is, rounded in any manner to allow easy rotation of the tool 100. As shown in FIG. 1, in one example embodiment the first handgrip 108 and the second handgrip 110 may be semi-cylindrical in shape and each handgrip 108, 110 may extend axially along a length of its respective arm 102, 104. That is, each semi-cylindrical handgrip 108, 110 may be disposed or formed anywhere between the two ends of its respective arm 102, 104 and may be of any suitable length. The handgrips 108, 110 in this example are semi-circular with respect to the transverse cross-section. Due to this semi-cylindrical shape, when the first arm 102 and the second arm 104 are compressed with respect to one another to the extent that contact surfaces of the first gripper 112 and the second gripper 114 come into contact, an operator of the tool 100 is able to axially rotate the tool 100 easily using the handgrips 108, 110 and a rolling motion between the operator's thumb and fingers grasping the handgrips 108, 110. Their rounded shape facilitates rotation between the pinched thumb and finger(s) lessening the required amount of rotation of the operator's wrist. This mechanism is further discussed in relation to FIG. 7.

The first gripper 112 is fitted to the distal end of the first arm 102 and has a contact surface on an inward facing side of the first gripper 112. The second gripper 114 is fitted to the distal end of the second arm 104 and has a contact surface on an inward facing side of the second gripper 114. As shown, in an open (uncompressed) state of the tool 100, the contact surfaces of the respective grippers 112, 114 face each other and are spaced apart. When the first arm 102 and the second arm 104 are compressed with respect to one another the first gripper 112 and the second gripper 114 come into contact at their contact surfaces. The first gripper 112 and the second gripper 114 may be made of silicone, for example, or any other material suitable for contact with the human eye. For hygienic purposes, the grippers 112, 114 may be single-use and/or disposable.

Figure 2:
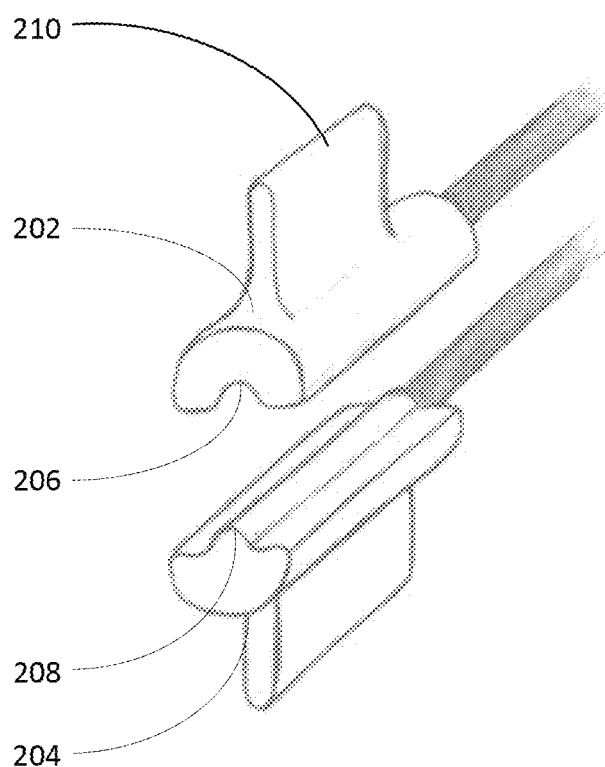
FIG. 2 is a perspective view of an example pair of disposable grippers for use with an eyelid eversion tool.

FIG. 2 is a perspective view of an example pair of disposable grippers for use with an eyelid eversion tool. The pair of disposable grippers include a first disposable gripper 202 having a contact surface on its inward facing side, and a second disposable gripper 204 having a contact surface on its inward facing side. The inward facing sides of the respective grippers 202, 204 face each other and are spaced apart when the tool is in an open position. In one example embodiment, the contact surface of the first disposable gripper 202 defines a groove 206 extending longitudinally along a length of the first disposable gripper 202 and the contact surface of the second disposable gripper 204 defines a raised tongue 208 extending longitudinally along a length of the second disposable gripper 204. In some examples, the tongue 208 is shaped and positioned to fit into the groove 206 when the contact surfaces come into contact thereby providing a secure grip. At least one of the first disposable gripper 202 and the second disposable gripper 204 has an extender tab 210 protruding from an outer side opposite its inward facing side. In the example shown in FIG. 2, each of the first disposable gripper 202 and the second disposable gripper 204 has an extender tab 210 protruding from its respective outer side opposite its respective inward facing side. In one embodiment, the protruding extender tab 210 extends longitudinally along at least a portion of the length of its respective gripper 202, 204. In some example embodiments, the extender tab 210 is shaped to narrow at an arcuate tip from a wider base.

Figure 3A:
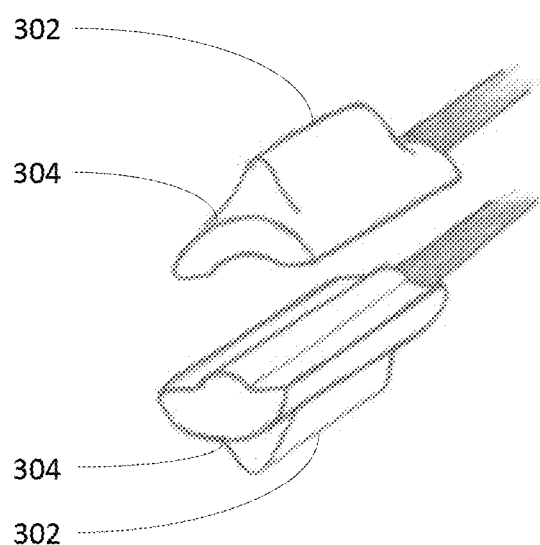
FIGS. 3A-3D are perspective views of other example pairs of disposable grippers for use with an eyelid eversion tool.
Figure 3B:
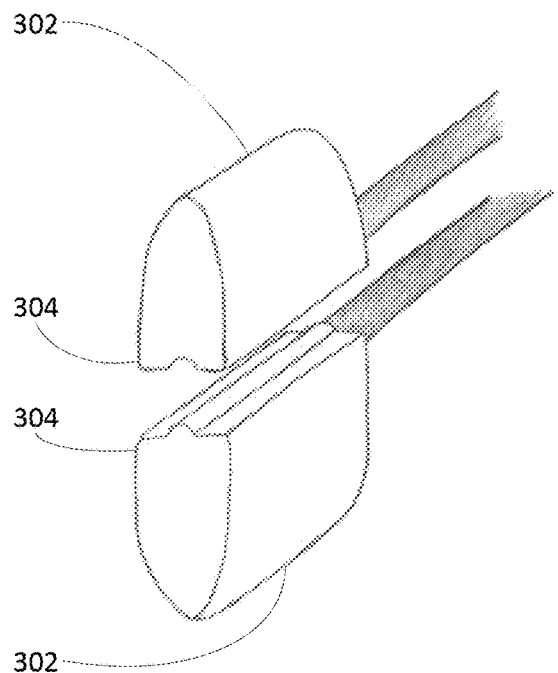

FIGS. 3A-3D are perspective views of alternate pairs of disposable grippers for use with an eyelid eversion tool. In the example of FIG. 3A, the pair of disposable grippers has wider proportions than those of the grippers in FIG. 2. Further, the extender tabs are of a different shape, yet still form an arcuate or curved tip 302 protruding from a wider base 304. Nevertheless, it will be appreciated that the extender tab need not necessarily have an arcuate or curved tip 302 and need not have a wider base 304 than its tip 302. The extender tab protrudes sufficiently far to provide a leverage point that bears against a patient's eyelid when rotating the eversion tool to evert the patient's eyelid, as will be described further below. As shown in the alternate disposable grippers of FIGS. 3B, 3C and 3D, the extender tabs need not necessarily be unique extensions protruding from the outer side of the grippers, but may, for example, be that portion of the grippers opposite their inward facing sides. Put differently, the extender tabs may be (integrally) formed longitudinally along the entire length of their respective grippers, between base 304 near the contact surfaces and tip 302.

Figure 3C:
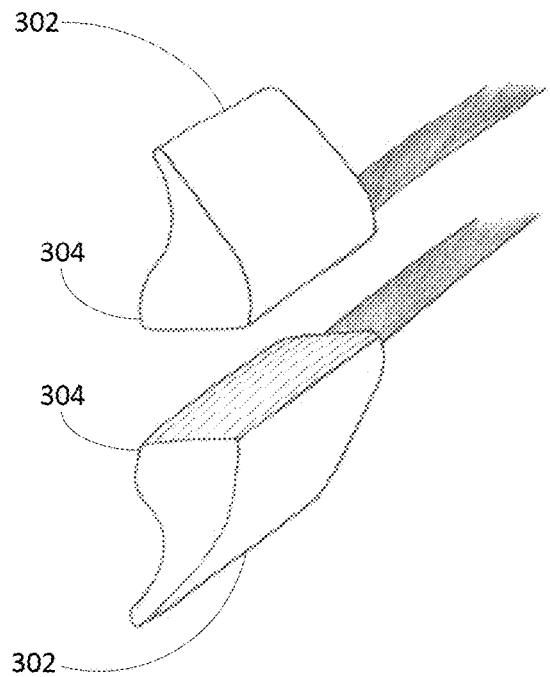
Figure 3D:
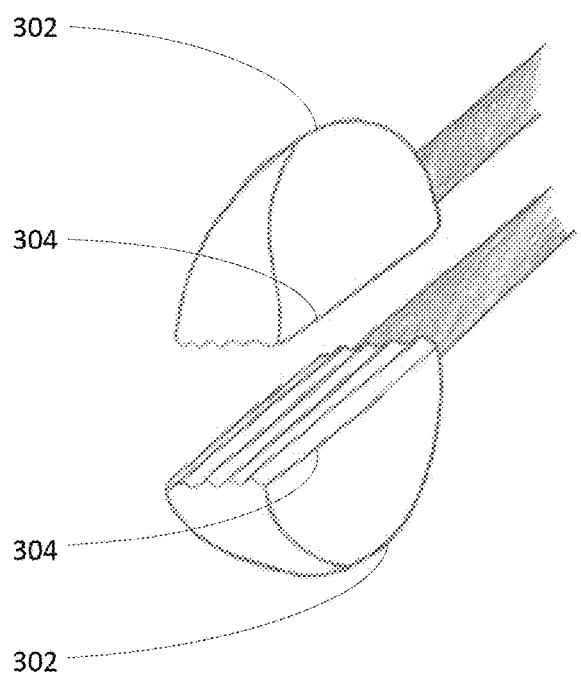

In some of the above examples, the respective contact surfaces feature a tongue-and-groove gripping surface (FIG. 3A, 3B); however, it will be appreciated that in other implementations different gripping surfaces may be used. For example, the contact surfaces may be flat (FIG. 3C). In some examples, the contact surfaces may be patterned, such as with ridges, cross-ridges, pits, nubs, or other such gripping patterns (FIG. 3D).

Any shape of disposable grippers may be utilized so long as their contact surfaces are cooperative to come into gripping contact.

Figure 4:
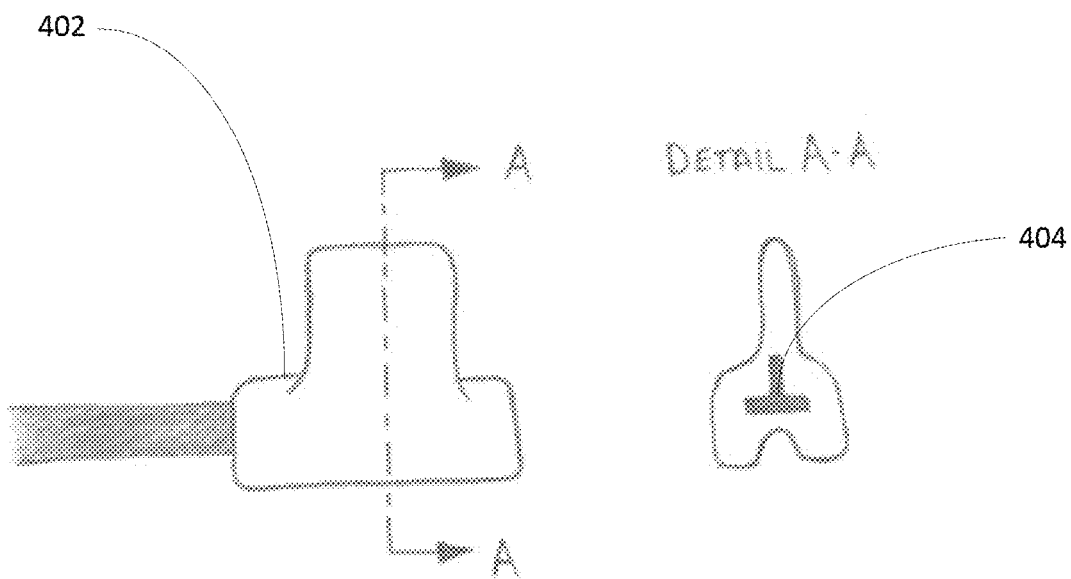
FIG. 4 is a side view of an example disposable gripper and cross-sectional detail view taken along line A-A.

FIG. 4 is a side view of an example disposable gripper and cross-sectional detail view taken along line A-A. The disposable gripper 402 is fitted to an eyelid eversion tool arm. As shown in cross-sectional detail A-A, the disposable gripper 402 has a keyed axial bore 404. The shape of the keyed axial bore 404 may be chosen as any suitable shape having at least one flat plane and/or right angles so as to prevent movement or rotation of the disposable gripper 402.

Figure 5:
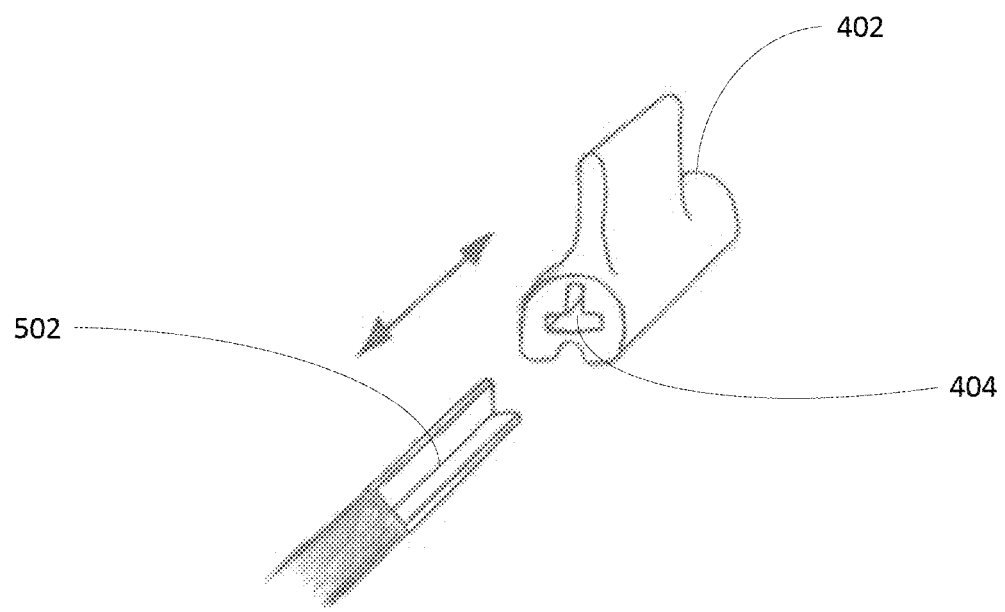
FIG. 5 shows the fitting and removal of the example disposable gripper of FIG. 4 from an eyelid eversion tool arm.

FIG. 5 shows the fitting and removal of the example disposable gripper of FIG. 4 from an eyelid eversion tool arm. A distal end of the tool arm has a corresponding keyed profile 502 matching the keyed axial bore 404 of the disposable gripper 402. As a result, the disposable gripper 402 may be friction fit onto the distal end of the arm. Removal of the disposable gripper 402 entails simply sliding the gripper 402 off the tool arm.

Figure 6:
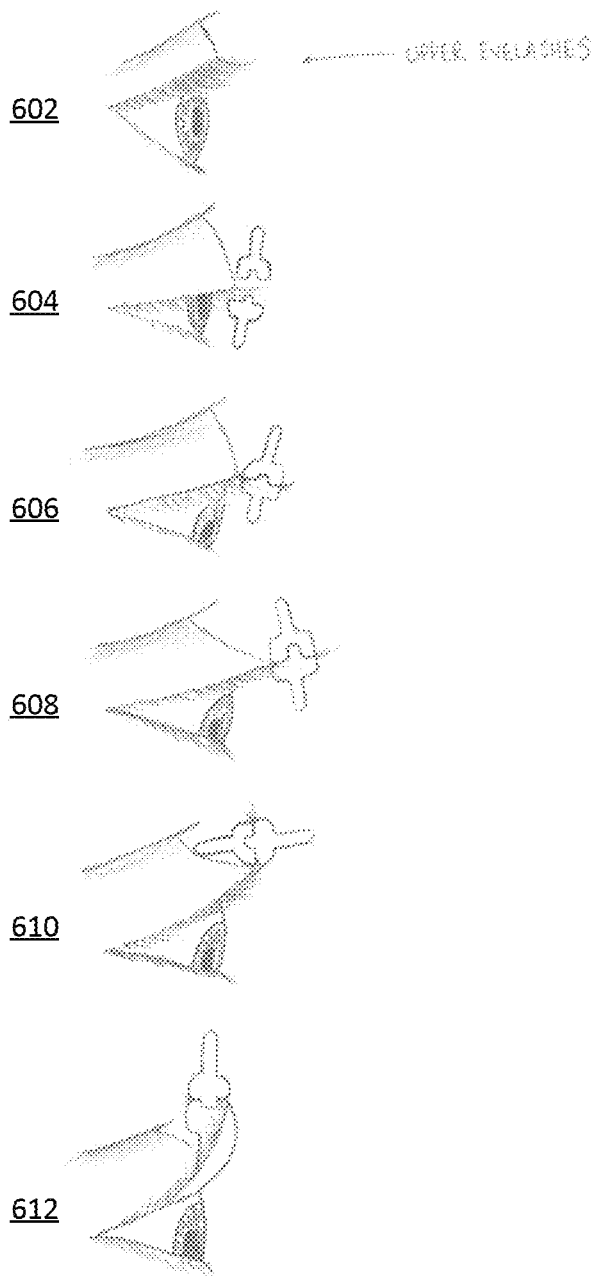
FIG. 6 is a side view of an example sequence depicting eversion of a subject's upper eyelid by an eyelid eversion tool.

FIG. 6 is a side view of an example sequence depicting eversion of a subject's upper eyelid by an eyelid eversion tool.

At step 602 a subject's open eye is shown and the upper eyelashes are indicated.

At step 604 the eyelid eversion tool is placed, in an uncompressed state, near a subject's eye to situate the subject's upper eyelashes between the first gripper and the second gripper.

At step 606 the eyelid eversion tool is compressed by squeezing the arms at the handgrips (not shown), with respect to one another, to securely grasp the subject's upper eyelashes.

At step 608 the eyelid eversion tool is pulled directly away from the subject thereby pulling the subject's eyelid away from the surface of the subject's eye.

At step 610, while pulling the tool away from the subject, the eyelid eversion tool is rotated at the handgrips causing the extender tab to press into the subject's upper eyelid.

At step 612 continuing to rotate the tool until the subject's eyelid is everted and the meibomian glands are exposed.

Figure 7:
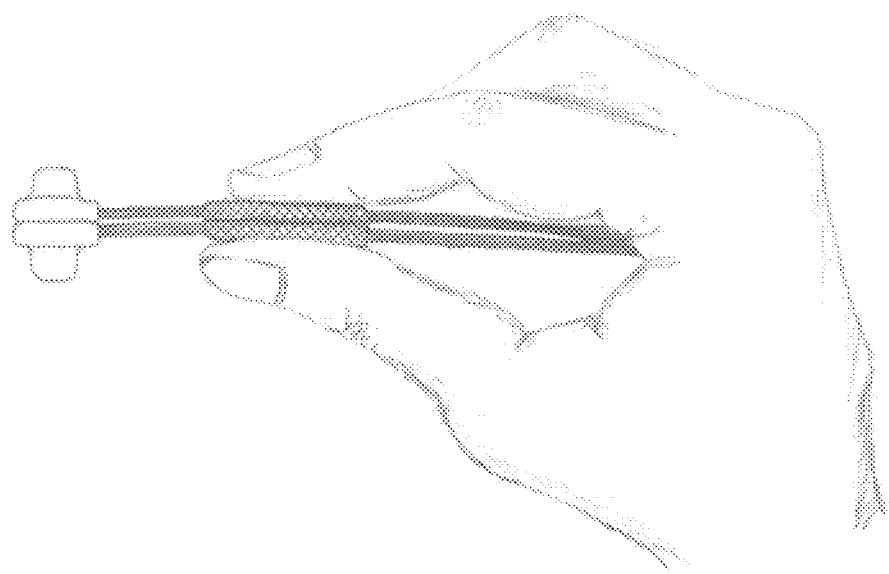
FIG. 7 illustrates the ergonomics of the eyelid eversion tool of FIG. 1 in use.
Figure 7:
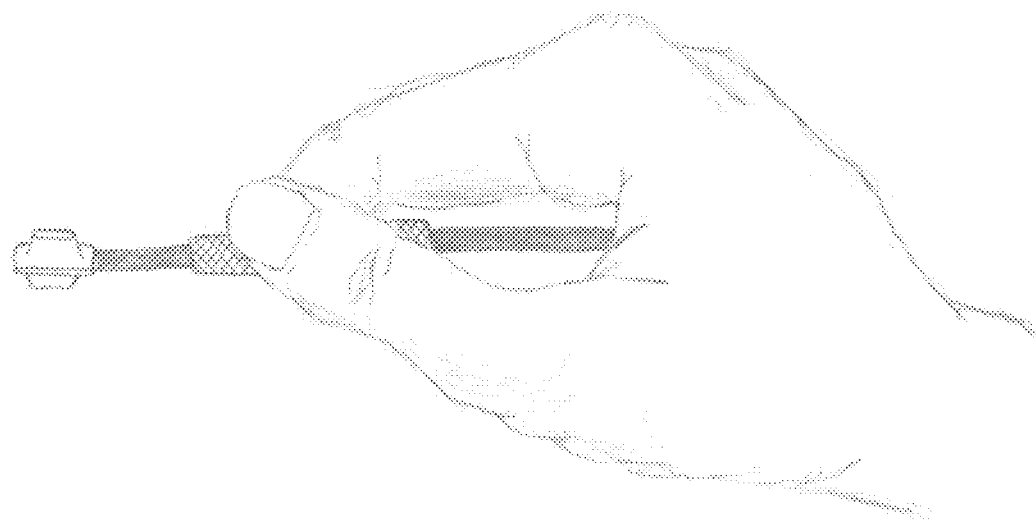

FIG. 7 illustrates the ergonomics of the eyelid eversion tool of FIG. 1 in use. As noted previously, the tool's first and second handgrip may be semi-cylindrical in shape and extend axially along a length of its respective arm. As shown, a user of the tool has squeezed the tool at the handgrips using his/her index finger and thumb. The arms of the tool are fully compressed with respect to one another and the grippers are in contact at their contact surfaces. In this initial position 700 the first and second handgrip have come together to form a cylindrical shape in the user's hand. It is this rounded shape of the handgrips together which provides ease of rotation to the user of the tool as he/she rotates the tool at the handgrips to a rotated position 710. As can be seen in FIG. 7 the tool may be used easily with one hand, thus freeing the user's other hand to manage a meibographer or other such task.

As noted, certain adaptations and modifications of the described embodiments can be made. Therefore, the above-discussed embodiments are considered to be illustrative and not restrictive.

What is claimed is:

1. An eyelid eversion tool comprising:
a first arm and a second arm extending along respective longitudinal axes from a common joint end, the first arm and the second arm each, respectively, having a distal end opposite the common joint end;
a first gripper configured to be friction fit to the distal end of the first arm, the first gripper having a contact surface on an inward facing side thereof; and
a second gripper configured to be friction fit to the distal end of the second arm, the second gripper having a contact surface on an inward facing side thereof,
wherein the contact surfaces face each other and are spaced apart, and the contact surfaces come into contact when the first arm and the second arm are compressed with respect to one another, and
wherein at least one of the first gripper and the second gripper has an extender tab aligned parallel to one of the respective longitudinal axes and protruding radially outward from an outward facing side of the at least one of the first gripper and the second gripper opposite its contact surface.

2. The eyelid eversion tool of claim 1, wherein the common joint end is fused and provides elastic deformation when the arms are compressed with respect to one another.

3. The eyelid eversion tool of claim 1, wherein the common joint end is hinged and resiliently biased in an open position to provide mechanical resistance when the arms are compressed with respect to one another.

4. The eyelid eversion tool of claim 1, further comprising a first handgrip on the first arm and a second handgrip on the second arm, the first handgrip and the second handgrip each, respectively, disposed between a distal end and the common joint end, wherein the first handgrip and the second handgrip are partially rounded to provide ease of rotation to a user of the tool.

5. The eyelid eversion tool of claim 4, wherein the first handgrip and the second handgrip are semi-cylindrical in shape and each handgrip extends axially along a length of its respective arm, and wherein the first handgrip and the second handgrip together form a cylindrical shape when the arms are compressed with respect to one another and the contact surfaces come into contact.

6. The eyelid eversion tool of claim 1, wherein each of the first gripper and the second gripper has a keyed axial bore, and wherein each of the first arm and the second arm has a corresponding keyed profile matching the keyed axial bore.

7. The eyelid eversion tool of claim 6, wherein the first gripper and the second gripper are made of silicone.

8. The eyelid eversion tool of claim 7, wherein the first gripper and the second gripper are disposable.

9. The eyelid eversion tool of claim 1, wherein the contact surface of the first gripper defines a groove extending longitudinally parallel to a first of the respective longitudinal axes along which the first arm extends and the contact surface of the second gripper defines a raised tongue extending longitudinally parallel to a second of the respective longitudinal axes along which the second arm extends, and wherein the tongue fits into the groove when the contact surfaces come into contact.

10. The eyelid eversion tool of claim 1, wherein the protruding extender tab is shaped to narrow at an arcuate tip from a wider base at the outward facing side of the at least one of the first gripper and the second gripper.

11. The eyelid eversion tool of claim 1, wherein the respective longitudinal axes define a plane and wherein the extender tab lies in the plane.

12. The eyelid eversion tool of claim 11, wherein the extender tab is centered in the plane.

13. A pair of grippers for use with an eyelid eversion tool, the eyelid eversion tool having a first arm and a second arm extending along respective longitudinal axes from a common joint end, each of the first arm and second arm having a distal end opposite the common joint end, the pair of disposable grippers comprising:
a first gripper having a first central axis and configured to be friction fit along a first of the respective longitudinal axes onto the distal end of the first arm and having a contact surface on a first side thereof; and
a second gripper having a second central axis and configured to be friction fit along a second of the respective longitudinal axes onto the distal end of the second arm and having a contact surface on a first side thereof,
wherein at least one of the first gripper and the second gripper has an extender tab aligned parallel its central axis and protruding radially from a second side opposite its contact surface.

14. The pair of grippers of claim 13, wherein each of the first gripper and the second gripper has a keyed axial bore extending longitudinally and shaped to receive a corresponding keyed profile of the distal end of the first arm or second arm when being friction fit.

15. The pair of grippers of claim 14, wherein the first gripper and the second gripper are made of silicone.

16. The pair of grippers of claim 13, wherein the contact surface of the first gripper defines a groove extending longitudinally along a length of the first gripper and the contact surface of the second gripper defines a raised tongue extending longitudinally along a length of the second gripper, and wherein the tongue fits into the groove when the contact surfaces come into contact.

17. The pair of grippers of claim 13, wherein the extender tab is shaped to narrow at an arcuate tip from a wider base at the second side of the at least one of the first gripper and the second gripper.

18. An eyelid eversion kit, comprising:
an eyelid eversion tool, including a first arm and a second arm extending along respective longitudinal axes from a common joint end, the first arm and the second arm each, respectively, having a distal end opposite the common joint end;
a first gripper configured to be friction fit onto the distal end of the first arm, the first gripper having a contact surface on an inward facing side thereof; and
a second gripper configured to be friction fit onto the distal end of the second arm, the second gripper having a contact surface on an inward facing side thereof,
wherein the contact surfaces face each other and are spaced apart, and the contact surfaces come into contact when the first arm and the second arm are compressed with respect to one another, and
wherein at least one of the first gripper and the second gripper has an extender tab aligned parallel one of the respective longitudinal axes and protruding radially outward from an outward facing side of the at least one of the first gripper and the second gripper opposite its contact surface.

19. The eyelid eversion kit of claim 18, wherein each of the first gripper and the second gripper has a keyed axial bore, and wherein each of the first arm and the second arm has a corresponding keyed profile matching the keyed axial bore.

* * * * *